United States Patent
Powers (10) Patent No.: US 8,145,300 B2
(45) Date of Patent: Mar. 27, 2012

(54) SIMPLIFIED BIPHASIC DEFIBRILLATOR CIRCUIT WITH MAKE-ONLY SWITCHING

(75) Inventor: Daniel J. Powers, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 669 days.

(21) Appl. No.: 12/300,162

(22) PCT Filed: May 10, 2007

(86) PCT No.: PCT/IB2007/051776
§ 371 (c)(1),
(2), (4) Date: Nov. 10, 2008

(87) PCT Pub. No.: WO2007/135600
PCT Pub. Date: Nov. 29, 2007

(65) Prior Publication Data
US 2009/0210022 A1 Aug. 20, 2009

Related U.S. Application Data

(60) Provisional application No. 60/747,337, filed on May 16, 2006.

(51) Int. Cl.
*A61N 1/39* (2006.01)
(52) U.S. Cl. .......................................................... 607/5
(58) Field of Classification Search ........................ 607/5
See application file for complete search history.

(56) References Cited

U.S. PATENT DOCUMENTS

| | | | | |
|---|---|---|---|---|
| 5,222,492 A | * | 6/1993 | Morgan et al. | 607/5 |
| 5,830,236 A | * | 11/1998 | Mouchawar et al. | 607/5 |
| 5,836,972 A | * | 11/1998 | Stendahl et al. | 607/5 |
| 5,906,633 A | | 5/1999 | Mouchawar et al. | |
| 5,908,442 A | | 6/1999 | Brewer et al. | |
| 6,208,896 B1 | * | 3/2001 | Mulhauser | 607/5 |
| 6,865,417 B2 | * | 3/2005 | Rissmann et al. | 607/5 |
| 2001/0031991 A1 | | 10/2001 | Russial | |

FOREIGN PATENT DOCUMENTS

| EP | 0546666 A2 | 10/1992 |
|---|---|---|
| GB | 2348139 A | 9/2000 |

* cited by examiner

*Primary Examiner* — Carl H Layno
*Assistant Examiner* — Luther Behringer
(74) *Attorney, Agent, or Firm* — W. Brinton Yorks, Jr.

(57) ABSTRACT

A biphasic pulse delivery circuit for a defibrillator includes two capacitors, a first one of which is charged and delivers the first phase of the biphasic pulse and a second one of which is charged and delivers the second phase of the biphasic pulse. At least a portion of the charge on the second capacitor is provided by the current flow through the patient during delivery of the first pulse phase. Switches are provided for initiating the first phase, initiating the second phase, and terminating the second phase. In an illustrated circuit a shunt circuit path is provided to at least partially charge the second capacitor from the first capacitor prior to delivery of the second phase of the biphasic pulse. The inventive circuit can be controlled entirely with switching devices that only need to be closed during pulse delivery.

12 Claims, 6 Drawing Sheets

SIMPLIFIED BIPHASIC DEFIBRILLATOR CIRCUIT WITH MAKE-ONLY SWITCHING

This invention relates to defibrillators for cardiac resuscitation, in particular, to defibrillators capable of delivering a biphasic pulse waveform.

Automatic external defibrillators ("AEDs") deliver a high-voltage impulse to the heart in order to restore normal rhythm and contractile function in patients who are experiencing arrhythmia, such as ventricular fibrillation ("VF") or ventricular tachycardia ("VT") that is not accompanied by a palpable pulse. There are several classes of defibrillators, including manual defibrillators, implantable defibrillators, and automatic external defibrillators. AEDs differ from manual defibrillators in that AEDs they are pre-programmed to automatically analyze an electrocardiogram ("ECG") rhythm to determine if defibrillation is necessary and to provide administration measures such as shock sequences and cardio-pulmonary resuscitation ("CPR") periods.

The current standard of care for AED resuscitation is the biphasic waveform. While the exact physiological mechanisms are not fully understood, it has been speculated that the second phase of the biphasic pulse causes a depolarization effect of the myocardial cells which have just been polarized by the first phase of the shock waveform, and that this depolarization in some way provides a more therapeutic waveform. In the application of a biphasic waveform the AED delivers high voltage charge to one of the electrode pads on the chest of the patient, which results in a flow of current from that pad to the second pad. At the end of this first phase an H-bridge of the high voltage output circuitry switches to reverse the applied voltage so that the remaining high voltage charge and current flow is delivered to the patient from the second electrode to the first. Clinical study and experience has shown that it is desirable to maintain a number of the parameters governing the biphasic waveform within predefined limits. For instance the positive (first) phase should have a duration which is not too short, and there should be a ratio of the first phase duration to the second phase duration which is within a predefined range. If a phase of the pulse is too short, it will be shorter than the cellular response time of the heart, the chronaxie time, thus limiting the effectiveness of the pulse. The decline of the starting voltage level to the level at the end of the first phase should not be too great, so that an appreciable amount of the delivered energy will remain for delivery during the second phase. There should also be a controlled relationship between the initial starting voltage level and the final pulse voltage level. Most of these parameters are affected by the patient chest impedance with patients of different impedances responding differently to a given pulse. Accordingly AEDs generally measure the patient chest impedance, either prior to delivery of the biphasic pulse or as the pulse begins, and tailor the operation of the AED high voltage circuit in consideration of the measured impedance.

Since AEDs are critically important when cardiac arrest occurs, it is desirable that their availability be as widespread as possible. While this objective has recently been aided by the approval for AED sales over-the-counter, it can also be advanced by the availability of low cost AEDs. One of the major expenses in AED manufacture is the high voltage circuitry, particularly the inductors and the switching devices of the H-bridge circuit, which must switch very large currents very rapidly, characteristics which cause these devices to be expensive to produce. Accordingly it is desirable for the designer of an AED high voltage circuit to reduce these costs where possible without affecting the safety or efficacy of the AED.

In accordance with the principles of the present invention a defibrillator high voltage circuit is provided which is simple and highly efficient and requires only the closure of switching devices during biphasic pulse delivery. The inventive circuit achieves efficiency through the use of two capacitors. As the main capacitor delivers the first pulse phase, current from the capacitor flows to and charges a second capacitor which delivers the second pulse phase. The commencement and cessation of pulse delivery is controlled by "make-only" switching devices, that is, devices which only need to close during pulse delivery.

Figure 1:
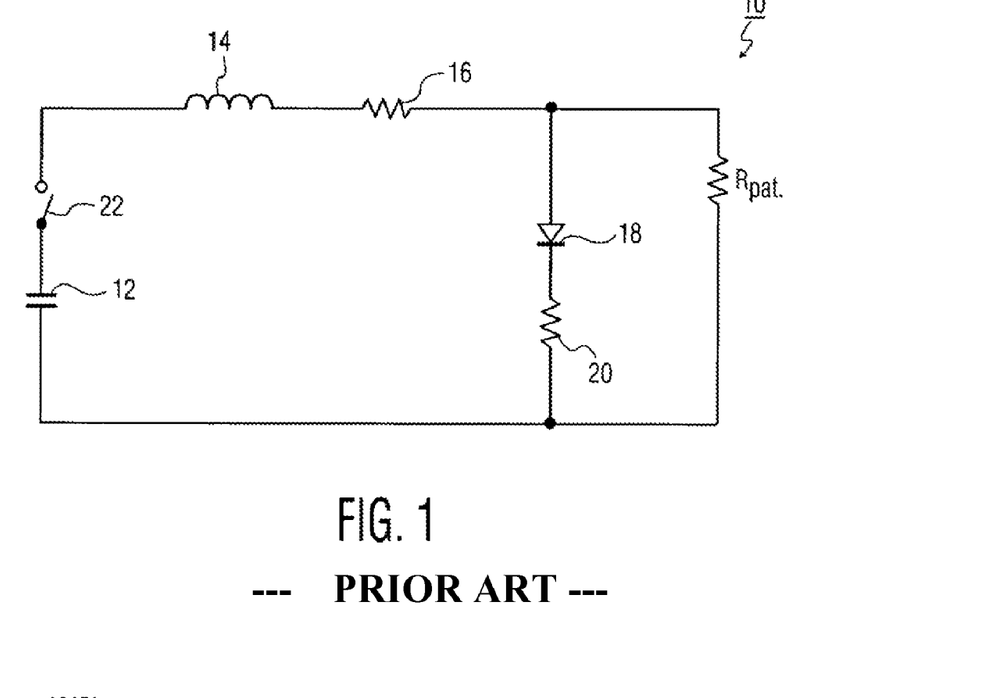
FIG. 1 illustrates a simple sinusoidal defibrillation pulse circuit of the prior art.
Figure 2:
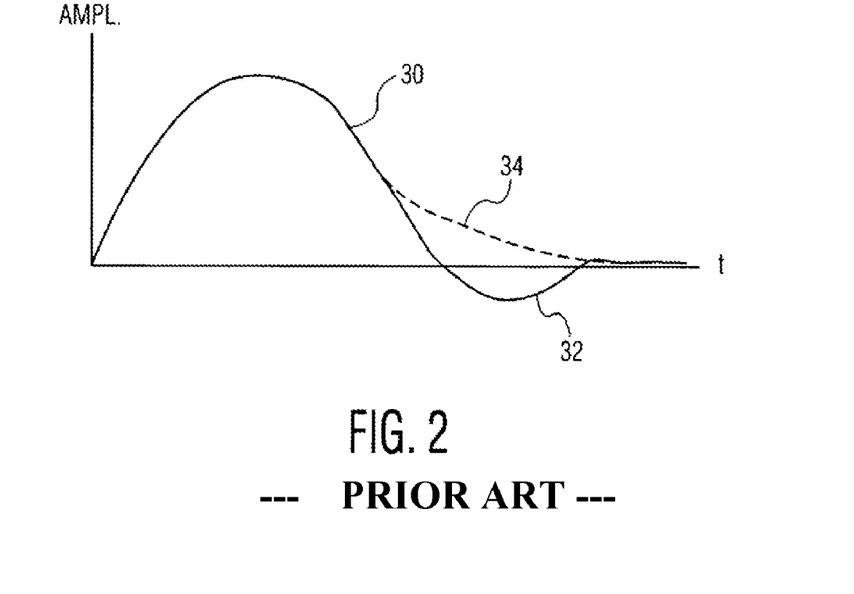
FIG. 2 illustrates waveforms which may be produced by the circuit of FIG. 1.

Referring first to FIG. 1, a defibrillation monophasic pulse circuit 10 is shown in schematic form. A storage capacitor 12 is charged by a high voltage supply (not shown) to deliver a defibrillating shock to a patient, represented by the patient impedance $R_{pat}$. Typical values for capacitor 12 are 10 µF and a rating of 7 kV. The shock is delivered to the patient through a large inductor 14 of, for example, 100 mH, which has a resistance represented by resistor 16. The patient impedance is shunted by a diode 18 and a small resistor 20. The shock is delivered by closing switch 22. When the circuit 10 exhibits critical damping, the waveform 30 will rise to a peak and then tail off slowly over a considerable time period as shown by the dashed line curve 34 of FIG. 2. When critically damped, a monophasic waveform is produced. The circuit 10 can also be configured to be underdamped, in which case the resulting waveform will rise, decline, undershoot the x-axis, and decay to the x-axis, effectively producing a sinusoidal biphasic waveform as shown by the solid line 32. A circuit of this sort can exhibit this biphasic characteristic over a wide range of patient impedances.

The defibrillation circuit of FIG. 1 has several advantages. It is simple with few components and hence inexpensive to implement. During the application of the waveform it is only necessary to close the switch 22, which can remain closed until pulse application is over. It is easier to close the switch of a high voltage circuit than it is to open a switch when large currents are flowing, which means that a less expensive "make-only" switch can be used. However there are several disadvantages with this circuit. One is the need for a large inductor, which adds undesired weight and takes up appreciable space in a small, portable AED. Another is the need to charge the capacitor 12 to a relatively high voltage for shock delivery. A third drawback is the inefficiency of the circuit, as an appreciable amount of energy is shunted by the shunt leg of the circuit and is not used to treat the patient. Typically, 30%-40% of the energy stored on the capacitor passes through the shunt leg and is not available to treat the patient.

Figure 3:
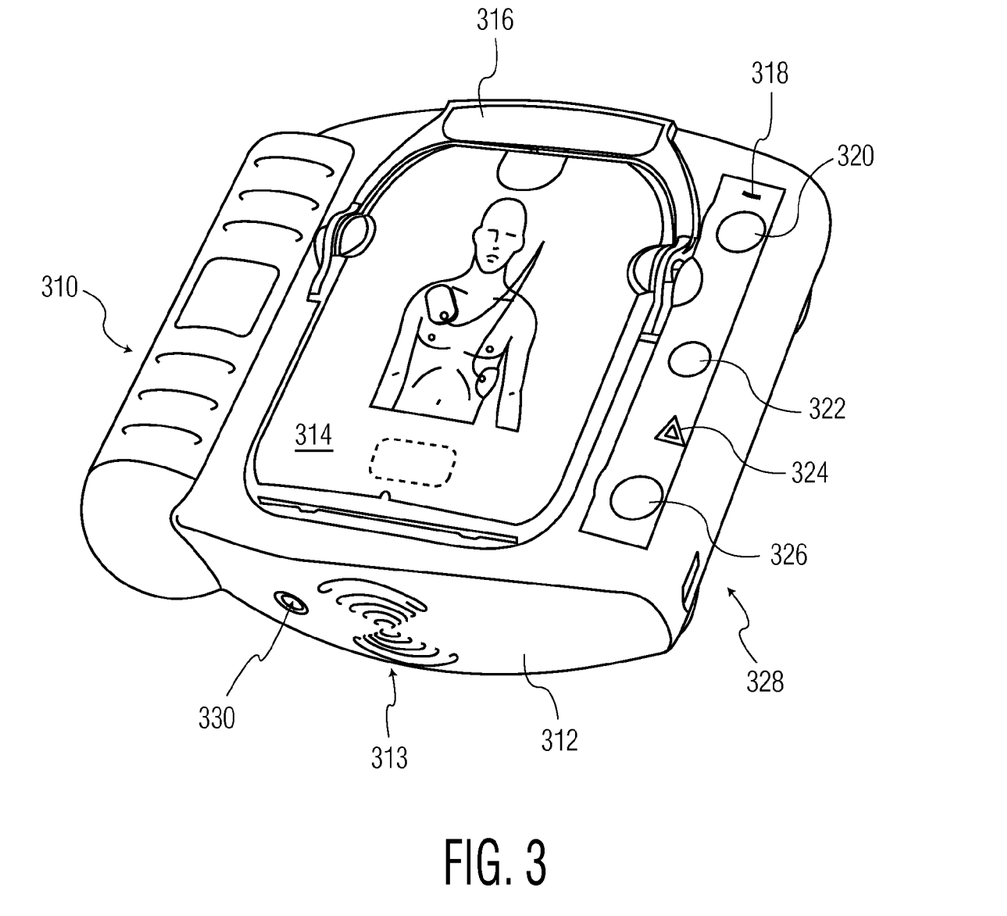
FIG. 3 illustrates an AED suitable for use with the high voltage circuit of the present invention.

FIG. 3 illustrates an AED 310 suitable for use with a high voltage circuit of the present invention. The AED 310 is housed in a rugged polymeric case 312 which protects the electronic circuitry inside the case and also protects the layperson user from shocks. Attached to the case 312 by electrical leads are a pair of electrode pads. In the embodiment of FIG. 3 the electrode pads are in a cartridge 314 located in a recess on the top side of the AED 310. The electrode pads are accessed for use by pulling up on a handle 316 which allows removal of a plastic cover over the electrode pads. A user interface is on the right side of the AED 310. A small ready light 318 informs the user of the readiness of the AED. In this embodiment the ready light blinks after the AED has been properly set up and is ready for use. The ready light is on constantly when the AED is in use, and the ready light is off or flashes in an alerting color when the OTC AED needs attention.

Below the ready light is an on/off button 320. The on/off button is pressed to turn on the AED for use. To turn off the AED a user holds the on/off button down for one second or more. An information button 322 flashes when information is available for the user. The user depresses the information button to access the available information. A caution light 324 blinks when the AED is acquiring heartbeat information from the patient and lights continuously when a shock is advised, alerting the user and others that no one should be touching the patient during these times. Interaction with the patient while the heart signal is being acquired can introduce unwanted artifacts into the detected ECG signal and should be avoided. A shock button 326 is depressed to deliver a shock after the AED informs the user that a shock is advised. An infrared port 328 on the side of the AED is used to transfer data between the AED and a computer. This data port finds use after a patient has been rescued and a physician desires to have the AED event data downloaded to his or her computer for detailed analysis. A speaker 313 provides voice prompts to a user to guide the user through the use of the AED to treat a patient. A beeper 330 is provided which "chirps" when the AED needs attention such as electrode pad replacement or a new battery.

Figure 4:
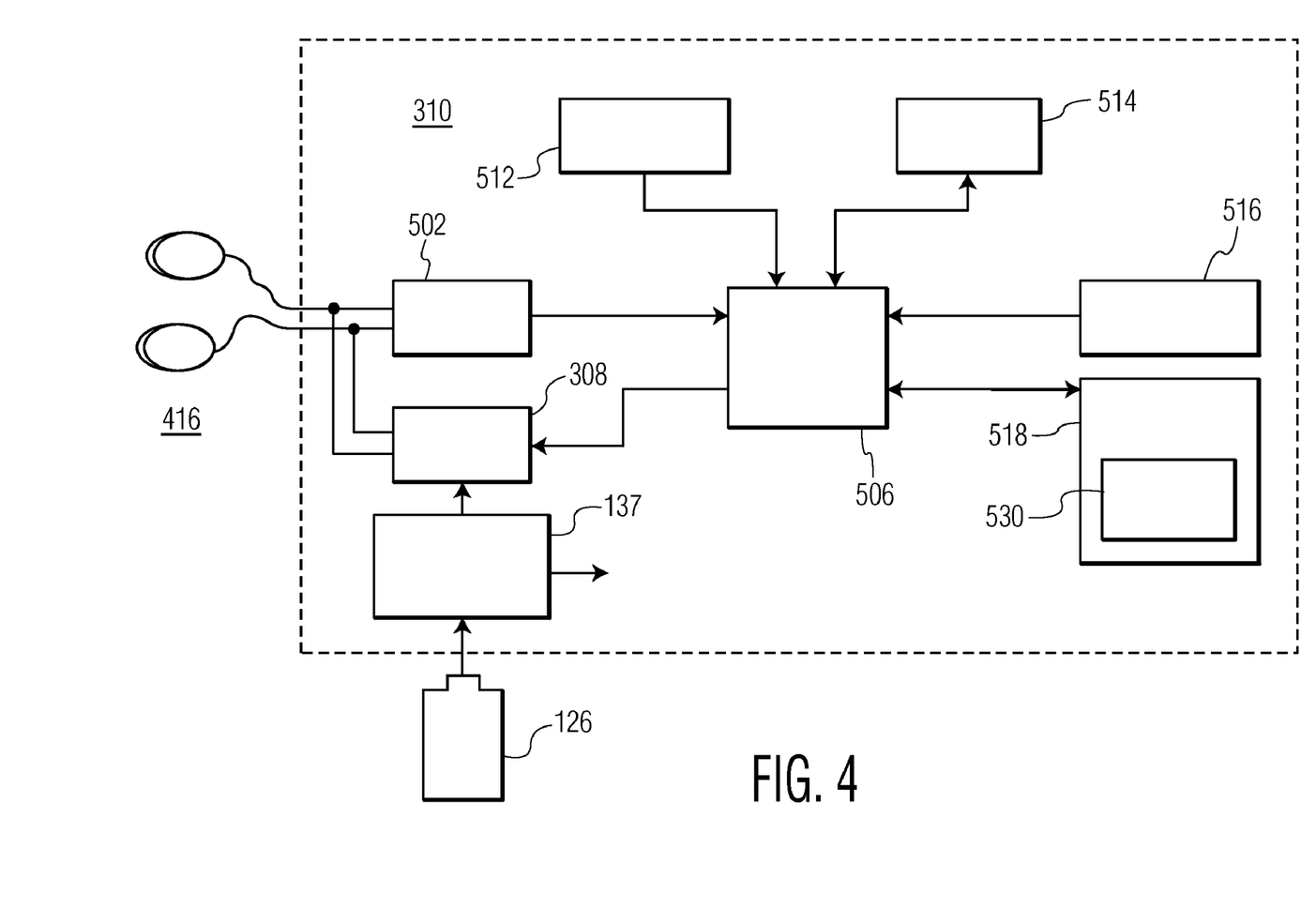
FIG. 4 illustrates in block diagram form the major functional subsystems of the AED of FIG. 3.

FIG. 4 is a simplified block diagram of the electronic components of AED 310 constructed in accordance with the principles of the present invention. An ECG front end 502 is connected to a pair of electrodes 416 that are attached to the chest of the patient being treated. The ECG front end 502 operates to amplify, buffer, filter and digitize an electrical ECG signal generated by the patient's heart to produce a stream of digitized ECG samples. The digitized ECG samples are provided to a controller 506 that performs an analysis to detect VF, shockable VT or other shockable rhythm. If a shockable rhythm is detected, the controller 506 sends a signal to HV (high voltage) delivery subsystem 308 to charge-up in preparation for delivering a shock. Pressing the shock button 326 then delivers a defibrillation shock from the HV delivery subsystem 308 to the patient through the electrodes 416. The controller can be configured to operate for defibrillation, cardiac monitoring, and CPR pause modes of operation.

The controller 506 is coupled to further receive input from a microphone 512 to produce a voice strip. The analog audio signal from the microphone 512 is preferably digitized to produce a stream of digitized audio samples which may be stored as part of an event summary 530 in a memory 518. A user interface 514 may consist of a display, an audio speaker 313, and front panel buttons previously discussed such as the on-off button 320 and shock button 326 for providing user control as well as visual and audible prompts. A clock 516 provides real-time clock data to the controller 506 for time-stamping information contained in the event summary 530. The memory 518 can be implemented either as on-board RAM, a removable memory card, or a combination of different memory technologies, and operates to store the event summary 530 digitally as it is compiled during treatment of the patient. The event summary 530 may include the streams of digitized ECG, audio samples, and other event data, as previously described.

The HV delivery subsystem is powered by high voltage supplied by a power management subsystem 137. The entire AED is powered by a battery 126 coupled to the power management subsystem 137. The power management subsystem includes a DC-to-DC converter to convert the low battery voltage to the high voltage required to charge the capacitor of the high voltage subsystem 308, and also supplies power of the appropriate voltages for the other processing and electronic components of the AED 310.

Figure 5:
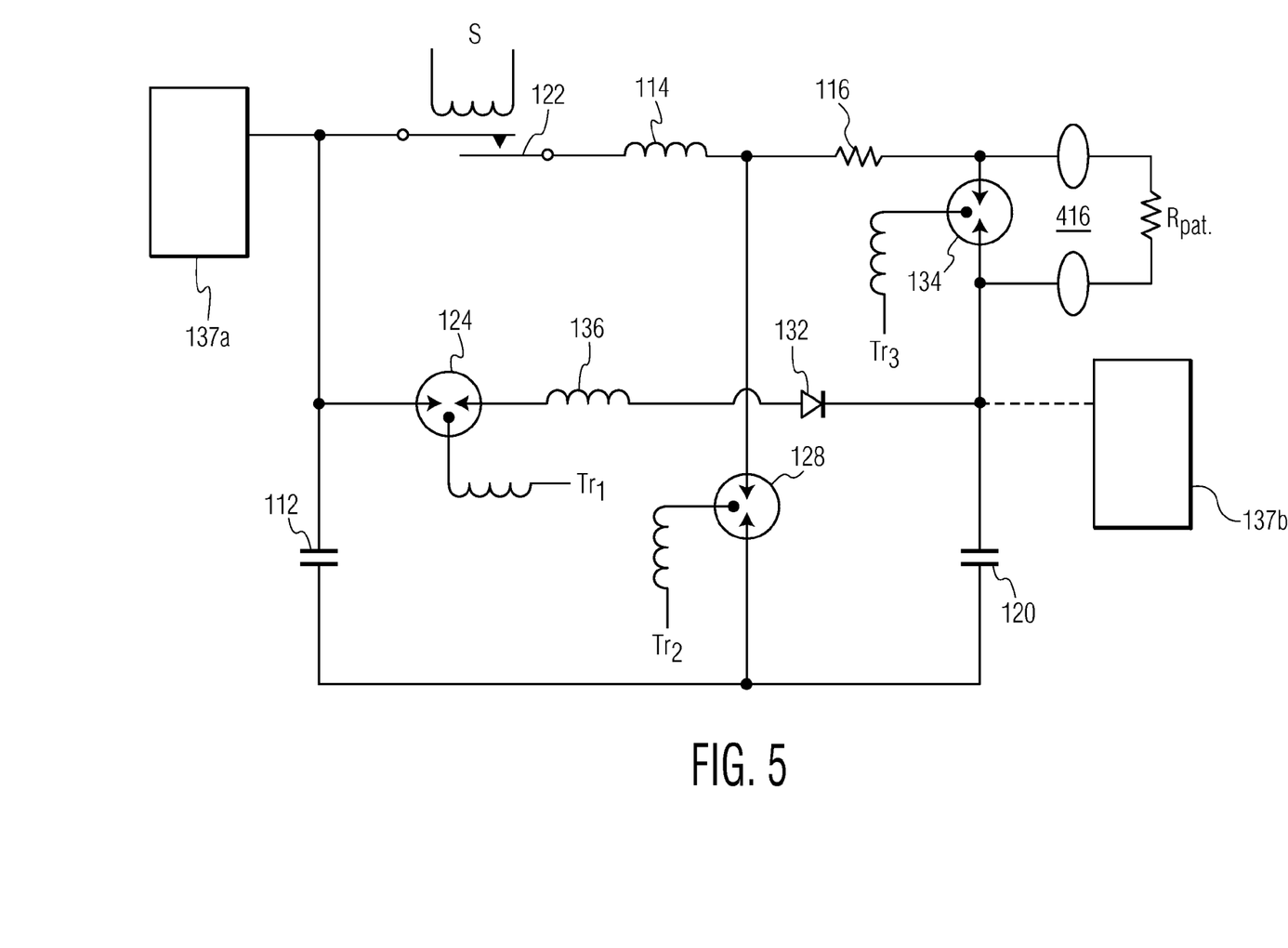
FIG. 5 illustrates a high voltage circuit constructed in accordance with the principles of the present invention.

A high voltage biphasic pulse circuit constructed in accordance with the principles of the present invention and suitable for use in the high voltage subsystem 308 of the defibrillator of FIG. 4 is schematically shown in FIG. 5. The circuit of FIG. 5 includes a main capacitor 112 which is charged for delivery of a defibrillating shock by a voltage $V_1$ from a $V_1$ supply 137a of the power management subsystem 137. Delivery of the shock is initiated by closure of a switch 122 in response to the shock delivery signal S. The switch 122 is coupled to a first one of the patient electrodes 416 by an inductor 114 and a small resistor 116. The inductor 114 limits the current delivered to a low impedance patient and the small resistor 116 limits current flow through the circuit leg in which it is used. Typical values for inductor 114 and resistor 116 are 35 mH and 2Ω, respectively.

A switch 134 is coupled across the two patient electrodes. A second capacitor 120 is coupled to the second patient electrode 416 for delivery of the second pulse phase. A charge delivery path from the main capacitor 112 to the second capacitor 120 includes a switch 124, a small inductor 136, and a diode 132. A typical value for inductor 136 is 2 mH. This inductor can be small because it is only switched into use for a short period of time as described below, and is subject to a relatively small voltage differential. The diode 132 assures unidirectional current flow in this path. A switch 128 is coupled between the junction of inductor 114 and resistor 116 and the reference conductive leg to which the two capacitors are coupled. Typical values for the two capacitors are 50 μF for the main capacitor 112 and 140 μF for the second capacitor 120. The main capacitor 112 can be a polypropylene capacitor which is of the same size as the capacitors now used in conventional AEDs, and the second capacitor can be a relatively inexpensive electrolytic capacitor stack.

In this example the switches 124, 128, and 134 are implemented by triggered spark gap devices. A spark gap device has two electrodes across which a potential is applied and when the potential reaches the critical level of the electrode spacing and dielectric between the electrodes, the device discharges as a spark is produced between the electrodes. These spark gap devices can be controllable discharged by prompting their discharge with a trigger pulse $Tr_1$, $Tr_2$, and $Tr_3$, respectively. The trigger pulse ionizes the gas in the spark gap, precipitating the discharge. The triggering pulse for some devices is an electrical pulse, and for others the triggering pulse excites an ultraviolet light source which ionizes the spark gap gas with ultraviolet energy. Advantages from use of the spark gap devices instead of conventional switches are low cost and the rapid switching which occurs when the spark gap devices are triggered.

When a biphasic pulse is delivered to a patient, the two phases of the waveform cause current flow in one direction between the two electrodes spanning the chest of the patient during the first phase of the pulse, and then in the other direction during the second phase. In theory, it should be possible to receive the current that flows in the first direction during the first phase, then flow it back in the opposite direction during the second phase, thereby making double use of the capacitor charge and producing a very efficient AED as a result. A circuit of the present invention produces an efficient AED by putting this theory to practice. In the operation of the circuit of FIG. 5 the main capacitor 112 is charged by the $V_1$ supply 137a in preparation for the delivery of a shock. The second capacitor 120 does not need to be charged during this preparation but, if desired, may be charged to a lesser level at this time as indicated by the $V_2$ supply 137b. During the first phase of the pulse the patient impedance sees the two capacitors coupled in series, with the patient impedance coupled between the two capacitors. When the rescuer presses the shock deliver button 136 the first phase of the biphasic pulse commences with a flow of current through switch 122, inductor 114, resistor 116, through the patient $R_{pat.}$, and returning to the second capacitor 120 which has its lower plate coupled in common with the main capacitor 112. Thus, the second capacitor 120 begins to be charged by charge delivered by the main capacitor 112 during the first phase of the biphasic pulse.

When it is desired to end the first phase of the pulse and deliver the second phase, the spark gap device 124 is triggered by trigger pulse $Tr_1$ and current from the main capacitor 112 is immediately shunted through the spark gap device, the inductor 136, and the diode 132 to rapidly charge capacitor 120 to a higher level. This shunting of current from the main capacitor, bypassing the patient impedance $R_{pat.}$, will bring the first phase of the biphasic pulse to an end. This flow of current is brief and can only continue until the voltage level of the main capacitor 112, already decreased from its initial charge level by delivery of the first pulse phase, approaches the rising voltage level of the second capacitor 120. The inductor 136 is small because of this short duration of charge transfer and because of the relatively small voltage differential of the two capacitors.

Following this brief shunting of charge from the main to the second capacitor, the second phase is commenced by triggering spark gap device 128. Current now flows to the patient in the opposite direction as the first phase as charge from the second capacitor 120 is delivered to the second patient electrode. The current path during this second phase of the biphasic pulse is from the second capacitor 120, through the patient, through the small resistor 116 and the spark gap device 128, and back to the capacitor 120. At the same time, the residual charge on the main capacitor 112 is dissipated by a current flow from capacitor 112, through switch 122, inductor 114, the spark gap device 128, and back to the capacitor 112. Thus, as the second phase of the pulse is delivered by the second capacitor, the main capacitor is discharged.

When it is desired to terminate the second phase of the biphasic pulse the spark gap device 134 is triggered by trigger pulse $Tr_3$. This spark gap device ends the delivery of energy to the patient by bypassing the patient electrodes. Residual charge on the capacitor 120 flows through the spark gap device 134, the small resistor 116, and the spark gap device 128 back to the second capacitor 120. The resistor 116 limits the peak current flow through this loop circuit during this discharge. After the remaining energy stored by the capacitors has been dissipated the switch 122 is opened (as are the other switches if conventional switching devices are used) and the circuit is ready to be charged for delivery of another biphasic pulse.

It is thus seen that a controlled biphasic pulse is delivered by a simple circuit without the complexity and expense of an H-bridge, and by the use of "make-only" switches which only have to close during pulse delivery. Such a circuit is highly suitable for a low cost AED.

A biphasic pulse delivery circuit of the type illustrated in FIG. 5 can deliver the following controlled biphasic pulses for the indicated patient impedances:

| Patient Impedance (Ω) | Energy Delivered (Joules) | Phase 1 Duration (msec) | Phase 2 Duration (msec) |
| --- | --- | --- | --- |
| 30 | 144 | 3.2 | 3.0 |
| 50 | 155 | 3.6 | 3.4 |
| 75 | 174 | 4.3 | 3.2 |
| 100 | 176 | 4.7 | 3.7 |
| 125 | 178 | 5.3 | 4.4 |
| 150 | 185 | 6.5 | 5.5 |
| 180 | 177 | 6.5 | 5.5 |

Figure 6:
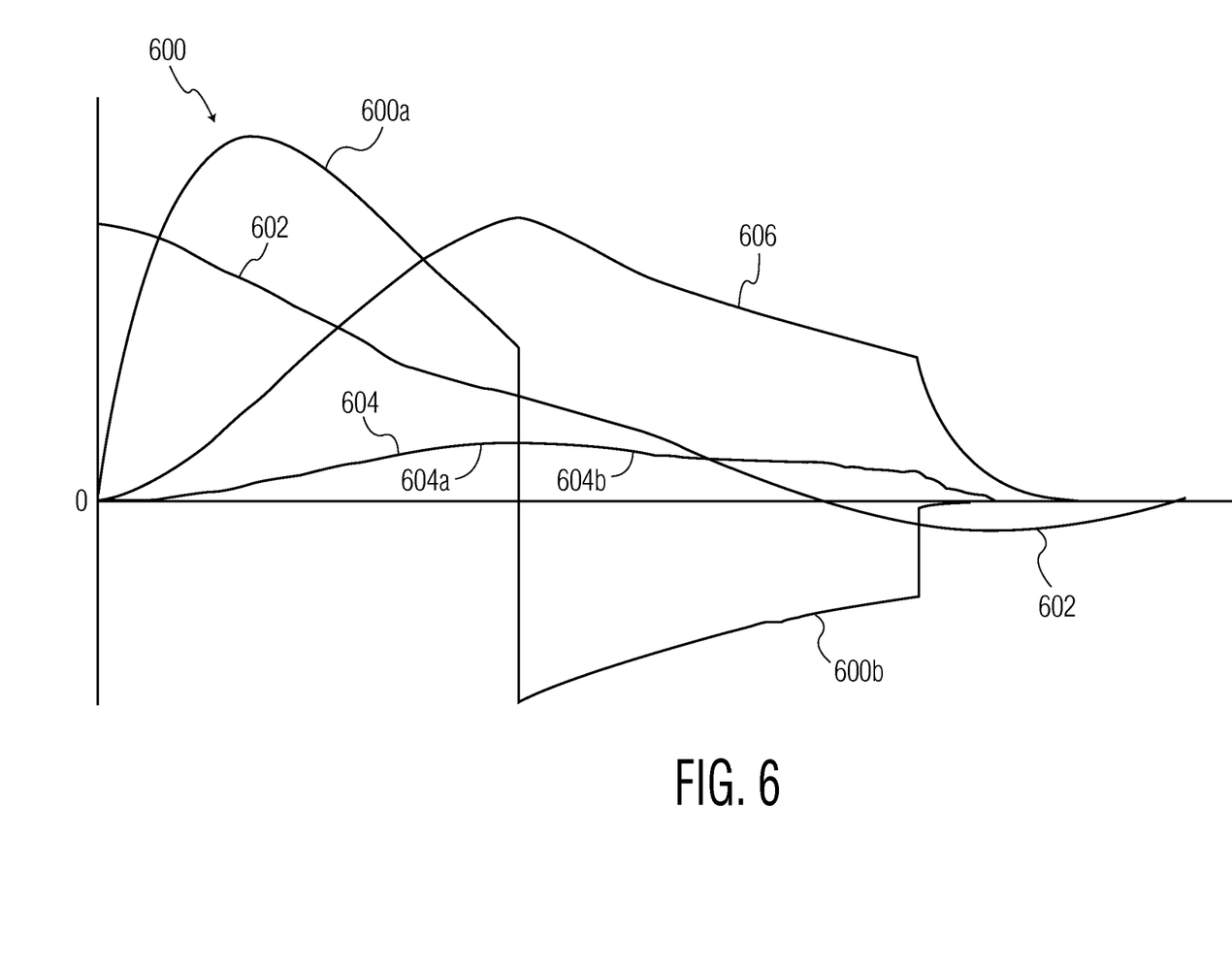
FIG. 6 illustrates waveforms explaining the operation of the high voltage circuit of FIG. 5 for a low impedance patient.

Performance characteristics of the circuit for a 30Ω patient are illustrated in FIG. 6. Curve 600 illustrates the biphasic pulse, including a first, positive phase 600a and a second, negative phase 600b. The charge delivered to the patient is indicated by curve 606, which is seen to rise very rapidly during the first phase and more slowly during the second phase. The portion of curve 606 is directed downward during the second phase in representation of the reverse flow of current during the second phase after the inflection point of the curve. Curve 602 illustrates the voltage of the main capacitor 112 which starts from its initially charged voltage level, declines during the first phase of 600a, then continues to discharge during the second phase as current is shunted to the second capacitor 120, going negative at the end of the pulse before finally being discharged. Curve 604 illustrates the voltage of the second capacitor 120 which, in this example, is not charged initially. The second capacitor is seen to develop voltage as it is charged by the flow of current from the first capacitor and through the patient during the first phase, reaching a peak when the second phase commences, and declining as the second phase is delivered by the second capacitor.

Figure 7:
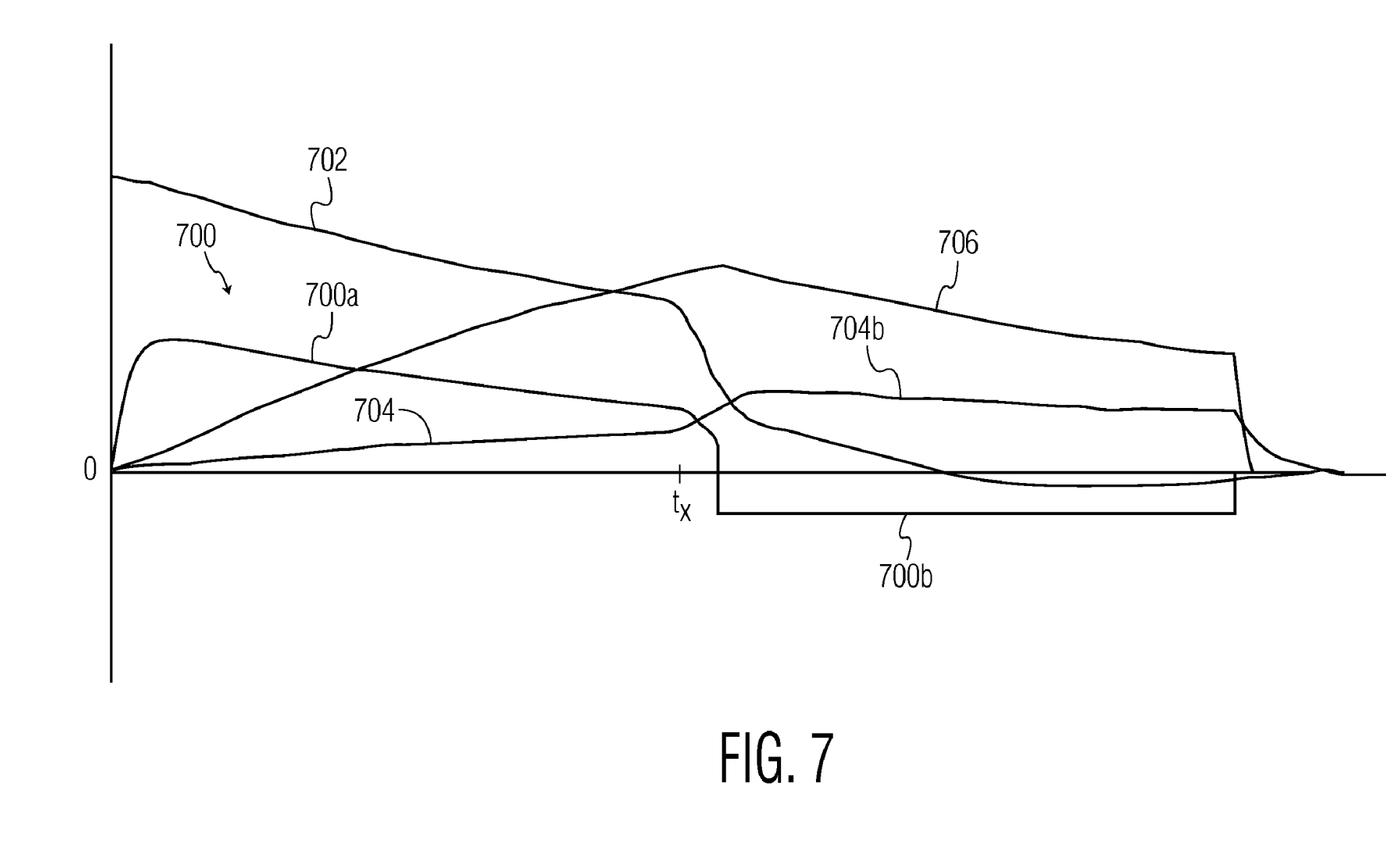
FIG. 7 illustrates waveforms explaining the operation of the high voltage circuit of FIG. 5 for a high impedance patient.

FIG. 7 illustrates the performance characteristics of the circuit for a 180Ω patient. It is seen that the initial rise of the first phase 700a of the biphasic pulse 700 attains a lower amplitude due to the greater patient impedance. This same characteristic is seen at the start of the second phase 700b. These curves more clearly illustrate the transition that occurs near the end of the first phase at time $t_x$ when switch 124 is closed to transfer charge to the second capacitor 120 in preparation for the start of the second phase 700b. The voltage on the main capacitor 112, illustrated by curve 702, is seen to steadily decline during the first phase until switch 124 is closed at time $t_x$, at which point the main capacitor voltage declines more rapidly as charge is transferred to the second capacitor. This is because less charge was delivered during the first phase as compared to FIG. 6 by reason of the greater patient impedance. A corresponding rapid increase of the voltage on the second capacitor 120 is seen for the second capacitor voltage curve 704, which thereafter declines during the second phase 704b as charge is delivered from the second capacitor during the second phase of the biphasic pulse. Curve 706 illustrates the cumulative charge delivered to the patient, with the negative slope during the second phase representing the change in polarity of the delivered waveform during the second phase. The second phase 700*b* ends and the remaining energy on the capacitors is dissipated when the switch 134 is closed.

It is thus seen that the biphasic pulse delivery circuit of the present invention is relatively simple as compared to the standard H-bridge circuit and can be controlled throughout the full range of patient impedances by the closure of "make-only" switches to produce a therapeutically effective biphasic pulse with the desired characteristics. The closure of switches causes each phase of the biphasic pulse to be started and terminated (truncated) at specifically controlled times so that a biphasic pulse tailored for the patient being treated and exhibiting a given patient impedance is delivered for therapy.

What is claimed is:

1. A high voltage defibrillator circuit for delivery of a biphasic pulse comprising:
   a high voltage source;
   a pair of patient electrodes;
   a first capacitor coupled to be charged by the high voltage source for the delivery of current during the first pulse phase, the first capacitor being controllably coupled to a first one of the pair of patient electrodes;
   a second capacitor coupled to a second one of the pair of patient electrodes to deliver current only during the second phase of the biphasic pulse;
   a plurality of switches coupled to control the durations of the phases of the biphasic pulse; and
   a controlling circuit disposed to selectively close each of the plurality of switches to deliver the biphasic pulse,
   wherein each of the plurality of switches remains closed at least to the end of the biphasic pulse.

2. The high voltage defibrillator circuit of claim 1, wherein the switches comprise make-only switches.

3. The high voltage defibrillator circuit of claim 1, wherein the plurality of switches includes a first switch which is closed to initiate delivery of the first pulse phase.

4. The high voltage defibrillator circuit of claim 3, wherein the plurality of switches includes a second switch which is closed to initiate delivery of the second pulse phase.

5. The high voltage defibrillator circuit of claim 4, wherein the plurality of switches includes a third switch which is closed to terminate delivery of the second pulse phase.

6. The high voltage defibrillator circuit of claim 4, wherein the plurality of switches includes a third switch which is closed to discharge at least one capacitor at the termination of the second pulse phase.

7. The high voltage defibrillator circuit of claim 5, wherein the plurality of switches include a fourth switch which is closed by the controlling circuit to transfer charge from the first capacitor to the second capacitor after a majority of the duration of the first pulse phase.

8. The high voltage defibrillator circuit of claim 1, wherein at least one of the switches comprises a triggered spark gap device.

9. A method for defibrillating a subject with an automatic external defibrillator comprising:
   determining that a defibrillating shock is advised; and
   delivering a biphasic pulse through a pair of patient electrodes by:
   charging a first capacitor from a high voltage supply;
   closing a first switch between the first capacitor and one of the patient electrodes to deliver a first pulse phase;
   transferring charge from the first capacitor to a second capacitor through the first switch and the one of the patient electrodes;
   closing a second switch to terminate the first pulse phase and initiate a second pulse phase from the second capacitor; and
   closing a third switch to terminate the second pulse phase.

10. The method of claim 9, wherein closing a second switch to terminate the first pulse phase and initiate a second pulse phase further comprises closing one switch to terminate the first pulse phase and closing another switch to initiate the second pulse phase.

11. The method of claim 9, wherein closing a third switch to terminate the second pulse phase further comprises dissipating the charge stored on the second capacitor.

12. The method of claim 9, wherein a plurality of the steps of closing a first, second and third switch further comprise triggering a spark gap device.

* * * * *